US012502299B2

(12) United States Patent
Soucy et al.

(10) Patent No.: US 12,502,299 B2
(45) Date of Patent: Dec. 23, 2025

(54) ORTHOTIC STRUCTURE SUPPORT BELT

(71) Applicant: B-TEMIA INC., St-Augustin-de-Desmaures (CA)

(72) Inventors: Francisco Soucy, St-Augustin-de-Desmaures (CA); Nathaniel Zoso, St-Augustin-de-Desmaures (CA)

(73) Assignee: WISTRON CORPORATION, New Taipei (TW)

(*) Notice: Subject to any disclaimer, the term of this patent is extended or adjusted under 35 U.S.C. 154(b) by 226 days.

(21) Appl. No.: 18/265,945

(22) PCT Filed: Dec. 6, 2021

(86) PCT No.: PCT/CA2021/051743
§ 371 (c)(1),
(2) Date: Jun. 7, 2023

(87) PCT Pub. No.: WO2022/120466
PCT Pub. Date: Jun. 16, 2022

(65) Prior Publication Data

US 2024/0122735 A1 Apr. 18, 2024

Related U.S. Application Data

(60) Provisional application No. 63/122,445, filed on Dec. 7, 2020.

(51) Int. Cl.
*A61F 5/02* (2006.01)
*A61F 5/01* (2006.01)

(52) U.S. Cl.
CPC .............. *A61F 5/02* (2013.01); *A61F 5/0102* (2013.01)

(58) Field of Classification Search
CPC ...... A61H 1/02; A61H 1/0237; A61H 1/0262; A61H 2003/007; A61F 2005/0183; A61F 5/02
See application file for complete search history.

(56) References Cited

U.S. PATENT DOCUMENTS

| | | | | |
|---|---|---|---|---|
| 2,573,866 | A | 11/1951 | Murphy | |
| 2010/0152636 | A1* | 6/2010 | Parks | A61F 5/028 602/33 |
| 2012/0271207 | A1 | 10/2012 | Schoen et al. | |
| 2016/0206029 | A1* | 7/2016 | Mills | A41C 1/10 |
| 2018/0161188 | A1* | 6/2018 | Zistatsis | A61H 1/024 |
| 2018/0338881 | A1* | 11/2018 | Ohtsubo | A61H 1/0262 |

OTHER PUBLICATIONS

The European search report dated Jul. 24, 2025, listed in related European patent application No. 21901742.3.

* cited by examiner

*Primary Examiner* — Keri J Nelson
(74) *Attorney, Agent, or Firm* — McClure, Qualey & Rodack, LLP

(57) ABSTRACT

There is disclosed an adjustable lower body orthotic structure supporting belt to be fitted to a user's morphology and pelvic tilt. The belt comprises at least one medial segment having an associated pivoting attachment that includes a securing mechanism to secure a lower body orthotic structure to the lateral with a variable sagittal orientation, a posterior support segment and a two-part securing segment connected via a locking mechanism to secure the belt to the user.

15 Claims, 5 Drawing Sheets

ORTHOTIC STRUCTURE SUPPORT BELT

CROSS-REFERENCE TO RELATED APPLICATIONS

This application claims the benefits of U.S. provisional patent application No. 63/122,445 filed on Dec. 7, 2020, which is herein incorporated by reference.

TECHNICAL FIELD

The present disclosure relates to an orthotic structure support belt.

BACKGROUND

Existing belts for the support of orthotic structures do not allow a rotation of the angle of attachment of the orthotic structure onto the belt in the sagittal plane. This can lead to pressure points on the user whose fitting requires a different angle of the orthotic structure. Furthermore, the orthotic structure support belt mostly requires many sizes to accommodate various waists lengths.

Accordingly, there is a need for orthotic structure support belt that allows rotation in the sagittal plane of the angle of attachment of the orthotic structure onto a supporting belt and adapts to the various physiognomies of users.

SUMMARY

The present disclosure provides a lower body orthotic structure supporting belt adjustable to be fitted to a user's morphology and pelvic tilt, the belt comprising:

- at least one medial segment configured to be located laterally in a sagittal plane and having an associated pivoting attachment to support a lower body orthotic structure with a variable sagittal orientation;
- a posterior support segment; and
- a frontal support system connected via a locking mechanism,
- wherein the pivoting attachment allows the lower body orthotic structure to maintain a vertical alignment while allowing the belt to adapt to the user's pelvic tilt.

The frontal support system can be, for example, a two-part securing segment, for example straps, connected via a locking mechanism, for example a side-release buckle.

The present disclosure provides a belt as above, comprising two medial segments each having a first end and a second end, the posterior support segment connecting to respective second ends of the two medial segments, and wherein each part of the two-part securing segment is connected to respective first ends of the two medial segments.

The present disclosure also provides a belt in which the pivoting attachment includes a pivoting base and a securing mechanism positioned thereon, the pivoting base rotatably, and optionally removably, engaging a corresponding medial segment circular receptacle provided on each medial segment. The pivoting attachment may be, for example, a first part of a two-part side-release buckle or a first part of a two-part magnetic clip. Advantageously, the medial segment is rigid in at least the sagittal plane with a portion under the pivoting attachment which is rigid in all planes.

The present disclosure further provides a belt which includes at least one length adjustment mechanism connecting the posterior support segment and a medial segment and/or one part of the two-part securing segment to a medial segment. The length adjustment mechanism may be composed of a variable length strap and hoop and may also be provided with locking tabs that are configured to be bent and overlap so as to lock the variable length strap at a desired length. The locking tabs may be, for example, Velcro™ strips. The at least one length adjustment mechanism may also include a pivot providing a degree of freedom adjustment in a frontal plane and a horizontal plane.

The present disclosure further provides a belt as above, wherein each of medial segments includes a pivoting element retainer, which may be, for example, a strap and a connector such that the strap passes over the pivoting attachment when secured to the connector, thus securing it in place.

BRIEF DESCRIPTION OF THE FIGURES

Embodiments of the disclosure will be described by way of examples only with reference to the accompanying drawings, in which.

Similar references used in different Figures denote similar components.

DETAILED DESCRIPTION

Generally stated, the non-limitative illustrative embodiment of the present disclosure provides an orthotic structure support belt with vertical attachments configured to support an orthotic structure regardless of a user's morphology or pelvic tilt. An example of an orthotic structure that can be supported by the present orthotic structure support belt is disclosed in International PCT Patent Application WO2011/123928 A1 entitled "LOAD DISTRIBUTION DEVICE FOR HUMAN JOINTS" published on 13 Oct. 2011.

Figure 1:
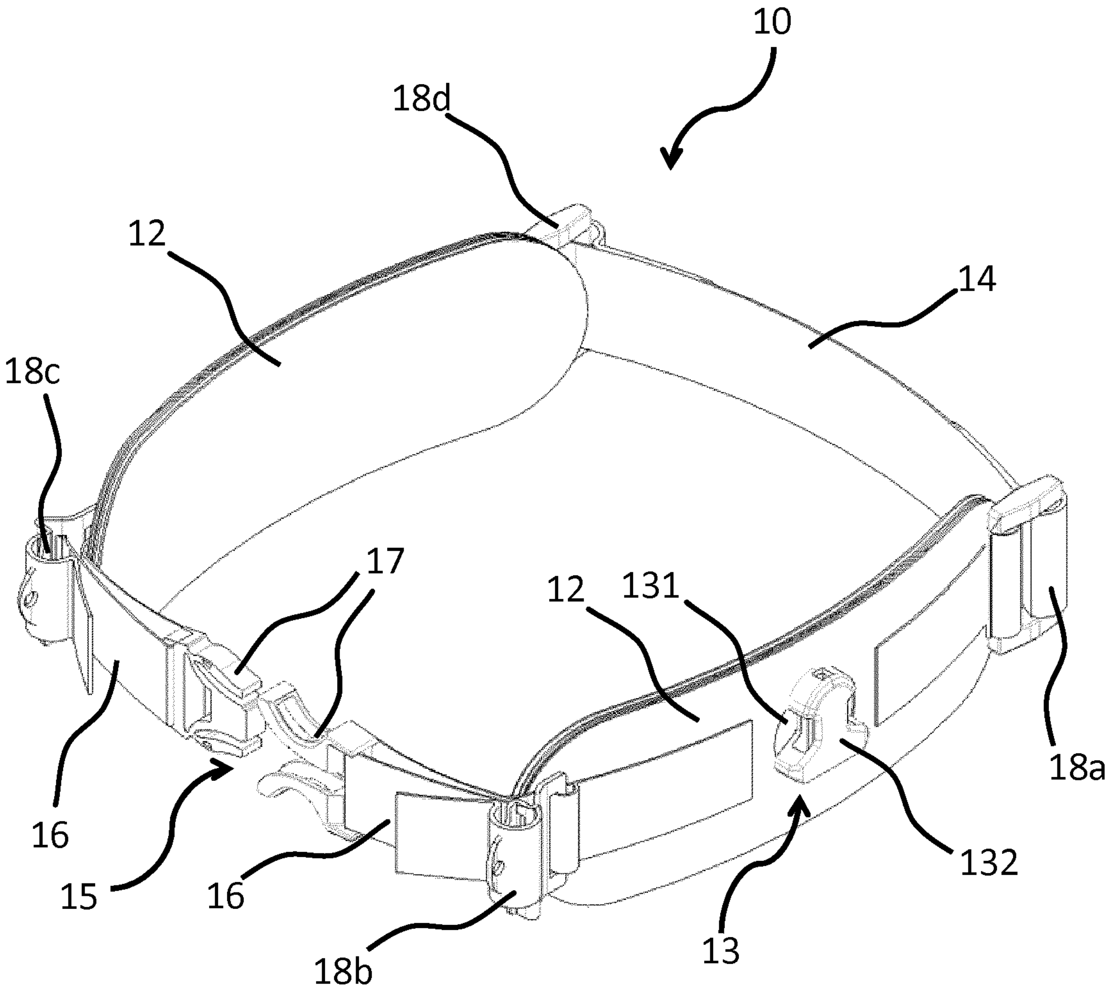
FIG. 1 is a perspective view of the orthotic structure support belt in accordance with an illustrative embodiment of the present disclosure.
Figure 2:
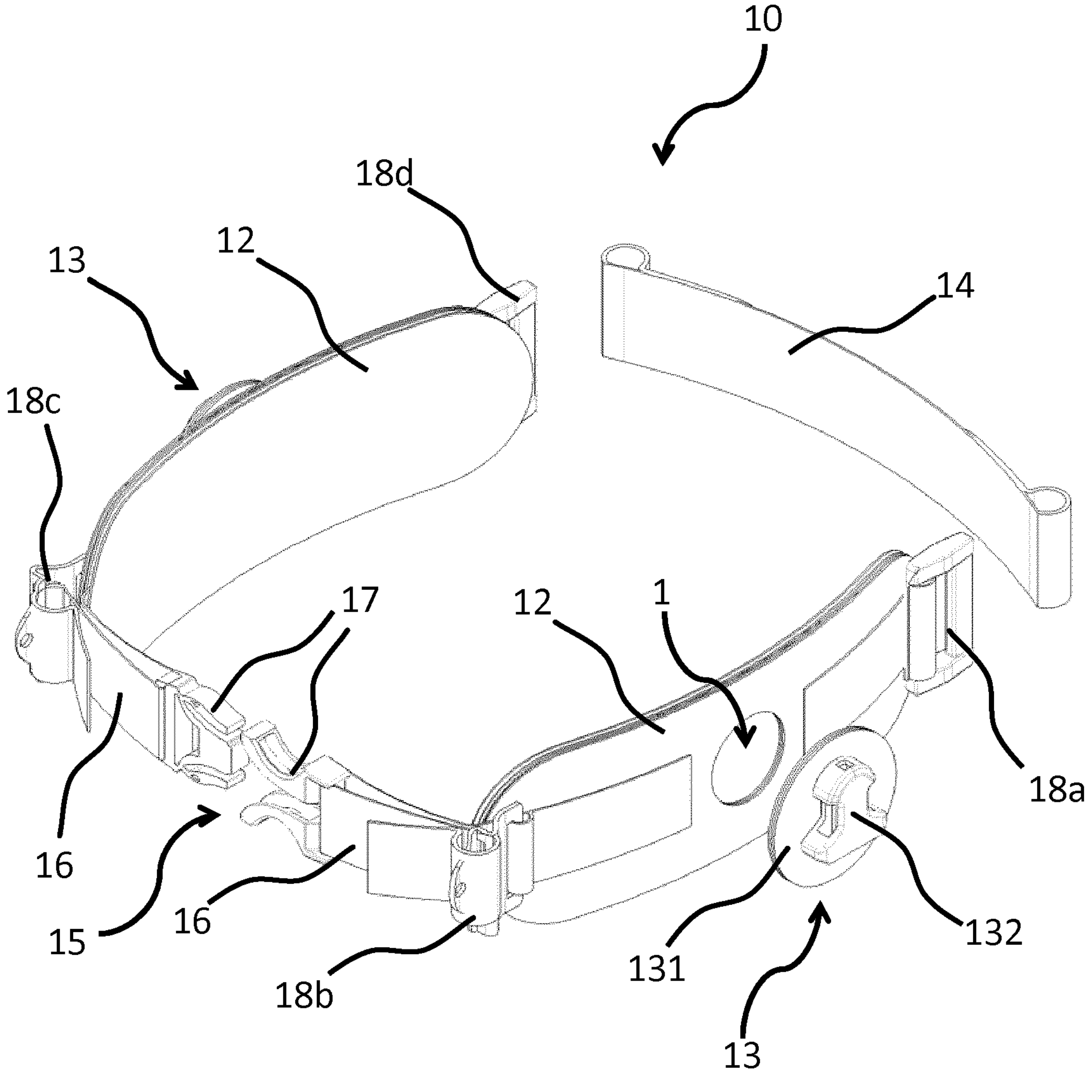
FIG. 2 is a perspective exploded view of the orthotic structure support belt of FIG. 1.

Referring to FIGS. 1 and 2, the orthotic structure support belt 10 generally includes a pair of medial segments 12, a posterior support segment 14 and a frontal support system 15.

Each medial segment 12 is provided with a pivoting attachment 13 formed of a pivoting base 131 and a securing mechanism 132 positioned thereon to connect a lower body orthotic structure to an associated medial segment 12 in a variable sagittal orientation. Advantageously, the part of the medial segment 12 under the pivoting base 131 is rigid in all planes with the remaining part of the medial segment 12 being rigid in at least the sagittal plane. The securing mechanism 132 may be, for example, a first part of a two-part side-release buckle with the securing mechanism 132 rotatably connected to the medial segment 12 via the pivoting base 131 engaged in a medial segment circular receptacle 1, allowing the positioning of the pivoting attachment 13 at variable sagittal angles. A second part of the two-part side-release buckle (not shown) is provided with the orthotic structure for attachment to the securing mechanism 132. Optionally, the pivoting attachment 13 may be removably secured to the medial segment 12. Optionally still, the medial segment 12 may be provided with padding in order to improve comfort.

The posterior support segment 14 and flexible frontal support system 15 connect to respective opposite ends of the medial segments 12 in order to form the orthotic structure support belt 10. The flexible frontal support system 15 is formed of two-part securing segment 16 connected via a locking mechanism 17, for example straps with a side-release buckle, in order to secure the orthotic structure support belt 10 around the waist of the user of the orthotic structure.

Optionally, the orthotic structure support belt 10 may also include one or more length adjustment mechanism 18*a*, 18*b*, 18*c*, 18*d* between the medial segments 12 and the posterior support segment 14 and/or straps 16 in order to adjust the circumference of the orthotic structure support belt 10 to the waist of users of various sizes. The length adjustment mechanisms 18*a*, 18*b*, 18*c*, 18*d* may be composed, for example, of a variable length strap and hoop. Optionally still, the length adjustment mechanisms 18*a*, 18*b*, 18*c*, 18*d* may also include a pivot providing a degree of freedom adjustment in the frontal and horizontal planes. between the medial segments 12 and the posterior support segment 14 and/or straps 16.

Figure 3:
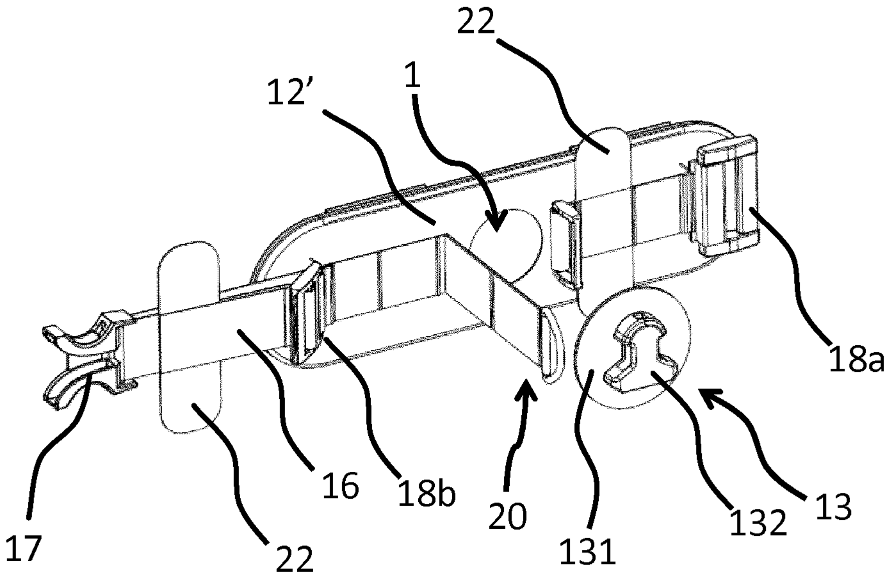
FIG. 3 is a perspective exploded view of a first alternative embodiment of the medial segment.
Figure 4:
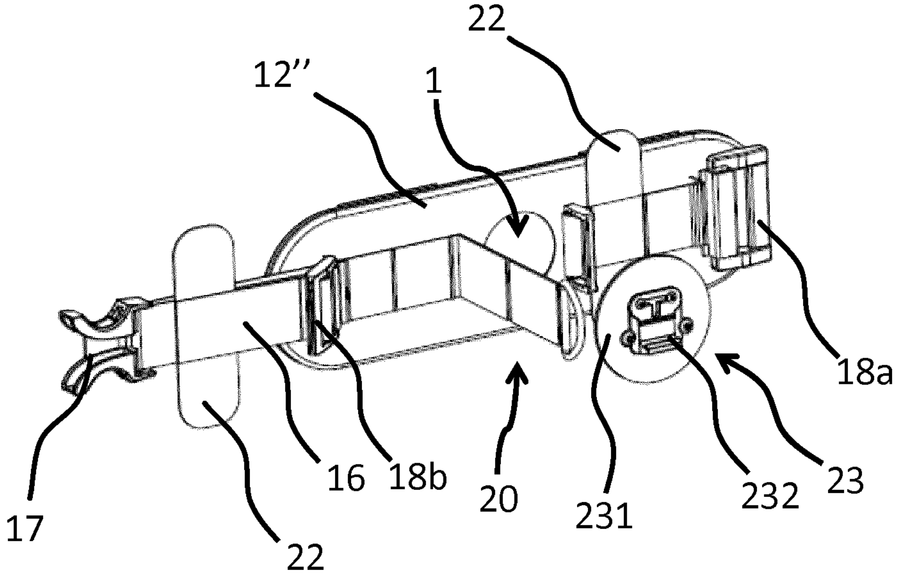
FIG. 4 is a perspective exploded view of a second alternative embodiment of the medial segment.

Referring now to FIGS. 3 and 4, there are show alternative embodiment of the medial segment 12' and 12", respectively. In the first alternative embodiment, illustrated in FIG. 3, the medial segment 12' includes a pivoting attachment retainer 20 for ensuring that the pivoting attachment 13 remain securely connected to the medial segment 12' and does not pop out from the medial segment circular receptacle 1. The pivoting attachment retainer 20 may be, for example, a strap and connector such that the strap passes over the pivoting attachment 13 when it is secured to the connector.

In the second alternative embodiment, illustrated in FIG. 4, the medial segment 12" is similar to the medial segment 12' of FIG. 3 but with an alternative pivoting attachment 23, the pivoting attachment retainer 20 ensuring that the pivoting attachment 23 remains securely connected to the medial segment 12" and does not pop out from the medial segment circular receptacle 1. The pivoting attachment 23 is formed of a pivoting base 231 and a securing mechanism 232 positioned thereon to connect a lower body orthotic structure to an associated medial segment 12 in a variable sagittal orientation. In this alternative embodiment, the securing mechanism 232 is a first part of a two-part magnetic clip with the securing mechanism 232 rotatably connected to the medial segment 12 via the pivoting base 231 engaged in the medial segment circular receptacle 1, allowing the positioning of the pivoting attachment 23 at variable sagittal angles. A second part of the two-part magnetic clip (not shown) is provided with the orthotic structure for attachment to the securing mechanism 232. Optionally, the pivoting attachment 23 may be removably secured to the medial segment 12.

Optionally, with reference to FIGS. 3 and 4, the one or more length adjustment mechanism 18*a*, 18*b*, 18*c*, 18*d* may be provided with locking tabs 22, for example Velcro™ strips, that may be bent and overlapped so as to lock a variable length strap of the corresponding adjustment mechanism 18*a*, 18*b*, 18*c*, 18*d* at a desired length.

Figure 5:
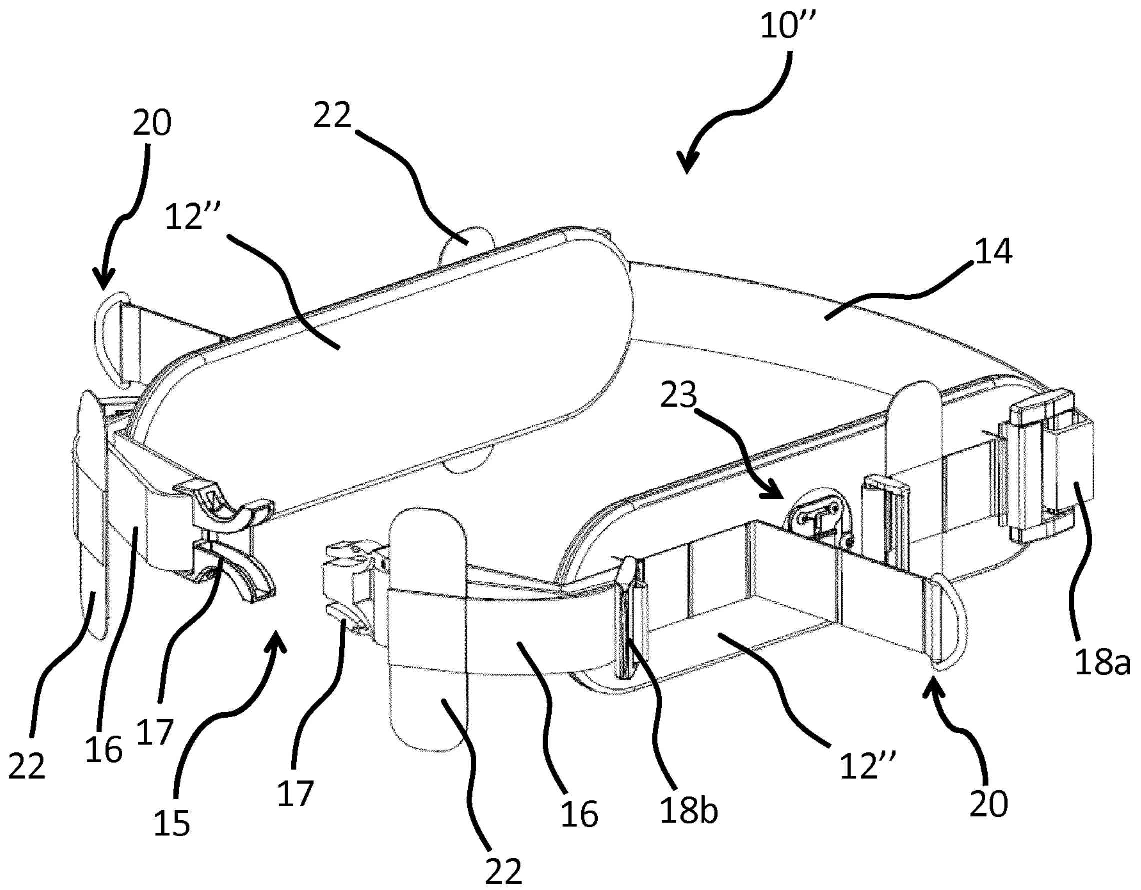
FIG. 5 is a perspective view of the orthotic structure support belt in accordance with an alternative embodiment in an unsecured configuration.
Figure 6:
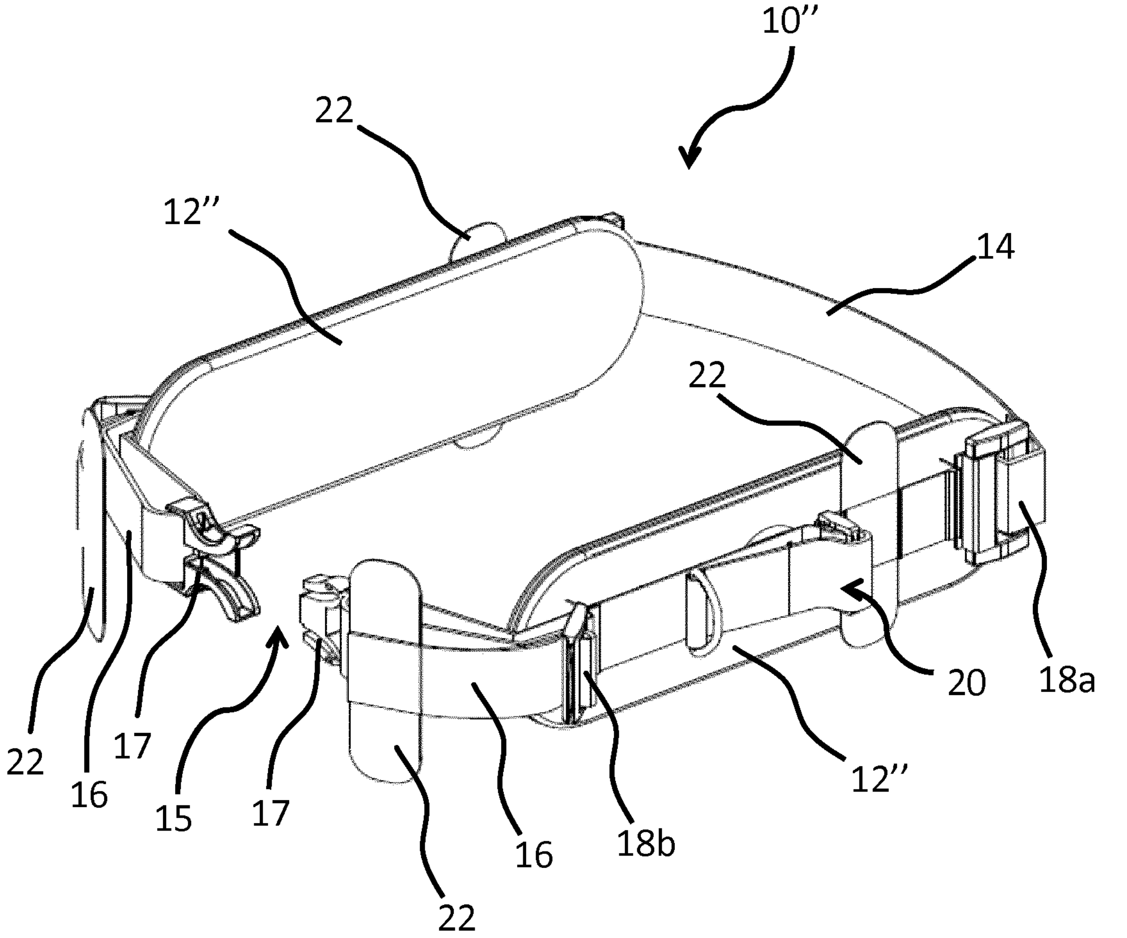
FIG. 6 is a perspective view of the orthotic structure support of FIG. 5 in a secured configuration.

Referring now to FIG. 5, there is shown the orthotic structure support belt 10" provided with medial segment 12" and locking tabs 22, with the pivoting attachment retainer 20 in an unsecured configuration, while FIG. 6 shows the orthotic structure support belt 10" with the pivoting attachment retainer 20 in a secured configuration, i.e. overlapping the pivoting attachment 13, 23.

It is to be understood that various configurations of the orthotic structure support belt 10 are possible, for example with various pivoting attachments 13, 23, with a single medial segment 12, with or without one or more of the length adjustment mechanisms 18*a*, 18*b*, 18*c*, 18*d*, pivoting attachment retainer 20 and/or locking tabs 22.

Although the present disclosure has been described by way of particular non-limiting illustrative embodiments and examples thereof, it should be noted that it will be apparent to persons skilled in the art that modifications may be applied to the present particular embodiment without departing from the scope of the present disclosure.

We claim:

1. A lower body orthotic structure supporting belt adjustable to be fitted to a user's morphology and pelvic tilt, the belt comprising:

two medial segment (12) each having a first end and a second end, and configured to be located laterally in a sagittal plane and having an associated pivoting attachment (13, 23) to support a lower body orthotic structure with a variable sagittal orientation, wherein the pivoting attachment (13, 23) allows the lower body orthotic structure to maintain a vertical alignment while allowing the belt to adapt to the user's pelvic tilt;

a posterior support segment (14), connecting to respective second ends of the two medial segments (12), wherein each part of the two-part securing segment (16) is connected to respective first ends of the two medial segments (12); and a frontal support system (15) connected via a locking mechanism (17);

wherein the pivoting attachment (13, 23) includes a pivoting base (131, 231) and a securing mechanism (132, 232) positioned thereon, the pivoting base (131, 231) rotatably engaging a corresponding medial segment circular receptacle (1) provided on each medial segment (12).

2. A belt according to claim 1, further comprising at least one posterior length adjustment mechanism (18*a*, 18*d*) connecting the posterior support segment (14) to a corresponding one of the second ends of the two medial segments (12).

3. A belt according to claim 2, wherein the at least one posterior length adjustment mechanism (18*a*, 18*d*) is composed of a variable length strap and hoop.

4. A belt according to claim 3, wherein the at least one posterior length adjustment mechanism (18*a*, 18*d*) is provided with locking tabs (22) that are configured to be bent and overlap so as to lock the variable length strap at a desired length.

5. A belt according to claim 2, wherein the at least one posterior length adjustment mechanism (18*a*, 18*d*) includes a pivot providing a degree of freedom adjustment in a frontal plane and a horizontal plane.

6. A belt according to claim 1, further comprising at least one frontal length adjustment mechanism (18*b*, 18*c*) connecting at least one part of the two-part securing segment (16) to a corresponding one of the respective first ends of the two medial segments (12).

7. A belt according to claim 6, wherein the first at least one frontal length adjustment mechanism (18*b*, 18*c*) is composed of a variable length strap and hoop.

8. A belt according to claim 7, wherein the at least one frontal length adjustment mechanism (18*b*, 18*c*) is provided with locking tabs (22) that are configured to be bent and overlap so as to lock the variable length strap at a desired length.

9. A belt according to claim 6, wherein the at least one frontal length adjustment mechanism (18*b*, 18*c*) includes a pivot providing a degree of freedom adjustment in a frontal plane and a horizontal plane.

10. A belt according to claim 1, wherein the two-part securing segment (16) and the locking mechanism (17) are straps and a side-release buckle, respectively.

11. A belt according to claim 1, wherein the at least one medial segment (12) is rigid in at least the sagittal plane with a portion under the pivoting attachment (13, 23) which is rigid in all planes.

12. A belt according to claim 1, wherein the posterior support segment (14) and the frontal support system (15) are flexible.

13. A lower body orthotic structure supporting belt adjustable to be fitted to a user's morphology and pelvic tilt, the belt comprising:

at least one medial segment (12) configured to be located laterally in a sagittal plane and having an associated pivoting attachment (13, 23) to support a lower body orthotic structure with a variable sagittal orientation;

a posterior support segment (14); and a frontal support system (15) connected via a locking mechanism (17), wherein the pivoting attachment (13, 23) allows the lower body orthotic structure to maintain a vertical alignment while allowing the belt to adapt to the user's pelvic tilt, the pivoting attachment (13, 23) is removably connected to the associated medial segment (12).

14. A lower body orthotic structure supporting belt adjustable to be fitted to a user's morphology and pelvic tilt, the belt comprising:

at least one medial segment (12) configured to be located laterally in a sagittal plane and having an associated pivoting attachment (13, 23) to support a lower body orthotic structure with a variable sagittal orientation;

a posterior support segment (14); and a frontal support system (15) connected via a locking mechanism (17), wherein the pivoting attachment (13, 23) allows the lower body orthotic structure to maintain a vertical alignment while allowing the belt to adapt to the user's pelvic tilt, and the pivoting attachment (13, 23) is selected from a group consisting of a first part of a two-part side-release buckle (132) and a first part of a two-part magnetic clip (232).

15. A lower body orthotic structure supporting belt adjustable to be fitted to a user's morphology and pelvic tilt, the belt comprising:

two medial segment (12) each having a first end and a second end, and configured to be located laterally in a sagittal plane and having an associated pivoting attachment (13, 23) to support a lower body orthotic structure with a variable sagittal orientation, wherein the pivoting attachment (13, 23) allows the lower body orthotic structure to maintain a vertical alignment while allowing the belt to adapt to the user's pelvic tilt;

a posterior support segment (14), connecting to respective second ends of the two medial segments (12), wherein each part of the two-part securing segment (16) is connected to respective first ends of the two medial segments (12); and a frontal support system (15) connected via a locking mechanism (17);

wherein each of the two medial segments (12) includes a pivoting element retainer (20), and is composed of a strap and a connector such that the strap passes over the pivoting attachment (13, 23) when secured to the connector.

* * * * *